(12) United States Patent
Nishitani et al.

(10) Patent No.: US 8,574,209 B2
(45) Date of Patent: Nov. 5, 2013

(54) ABSORBENT ARTICLE HAVING A TOP SHEET WITH A LOWER APPARENT DENSITY REGION

(75) Inventors: Kazuya Nishitani, Kanonji (TW); Minako Sagisaka, Kanonji (TW)

(73) Assignee: Unicharm Corporation, Ehime (JP)

( * ) Notice: Subject to any disclaimer, the term of this patent is extended or adjusted under 35 U.S.C. 154(b) by 268 days.

(21) Appl. No.: 12/991,731

(22) PCT Filed: Apr. 8, 2009

(86) PCT No.: PCT/JP2009/057544
§ 371 (c)(1),
(2), (4) Date: Jan. 26, 2011

(87) PCT Pub. No.: WO2009/139255
PCT Pub. Date: Nov. 19, 2009

(65) Prior Publication Data
US 2011/0125120 A1    May 26, 2011

(30) Foreign Application Priority Data

May 15, 2008   (JP) ................................ 2008-128730

(51) Int. Cl.
*A61F 13/15* (2006.01)
*A61F 13/20* (2006.01)
(52) U.S. Cl.
USPC ............................. 604/385.101; 604/385.01
(58) Field of Classification Search
USPC .................... 604/365–367, 378–380, 385.01, 604/385.101
See application file for complete search history.

(56) References Cited

U.S. PATENT DOCUMENTS

| | | |
|---|---|---|
| 6,362,391 B1 * | 3/2002 | Mizutani et al. .............. 604/379 |
| 6,802,932 B2 | 10/2004 | Kudo et al. |
| 2007/0073253 A1 | 3/2007 | Miyama et al. |

FOREIGN PATENT DOCUMENTS

| | | |
|---|---|---|
| JP | 10-94558 | 4/1998 |
| JP | 11-189961 | 7/1999 |
| JP | 2000-135239 | 5/2000 |
| JP | EP 0 997 124 | 5/2000 |
| JP | 2000-262558 | 9/2000 |
| JP | 2003-235894 | 8/2003 |
| JP | 2003-339761 | 12/2003 |
| JP | 2004113489 A | 4/2004 |

OTHER PUBLICATIONS

Extended Search Report 09746462.2-22124 issued Aug. 9, 2011.

* cited by examiner

*Primary Examiner* — Michele M Kidwell
(74) *Attorney, Agent, or Firm* — Lowe, Hautptman & Ham

(57) ABSTRACT

An absorbent article includes liquid-permeable top sheet, a liquid-impermeable back sheet, and an absorber sandwiched between the top sheet and back sheet, wherein the top sheet is composed of a nonwoven fabric, and the region of the top sheet that contacts the site of discharge is the low density section of the nonwoven fabric with a lower apparent density than the other regions of the top sheet. The thickness of the low density section of the top sheet is larger than the thickness of the sections other than the low density section of the top sheet, and the basis weight of the low density section of the top sheet is equal to the basis weight of the sections other than the low density section of the top sheet.

8 Claims, 10 Drawing Sheets

ABSORBENT ARTICLE HAVING A TOP SHEET WITH A LOWER APPARENT DENSITY REGION

CROSS-REFERENCE TO RELATED APPLICATIONS

The present Application is based on International Application No. PCT/JP2009/057544, filed on Apr. 8, 2009, which in turn corresponds to Japanese Application No. 2008-128730, filed on May 15, 2008, and priority is hereby claimed under 35 USC §119 based on these applications. Each of these applications are hereby incorporated by reference in their entirety into the present application.

TECHNICAL FIELD

The present invention relates to an absorbent article for sanitary napkins or disposable diapers.

BACKGROUND ART

Absorbent articles employing liquid-permeable top sheets composed of bulked fabrics interspersed with stamped thermal compression areas are known (Japanese Unexamined Patent Publication No. 2000-262558). Such absorbent articles that are interspersed with stamped thermal compression areas allow excreted urine to be rapidly absorbed into the top sheet, while also reducing contact area with the skin and minimizing wetness felt by the skin, due to differences in capillarity. The stamped thermal compression areas are interspersed across the entire surface of the top sheet, and the top sheet does not differ between the regions in contact with the site of discharge and the other regions. That is, with the exception of the stamped thermal compression areas, the top sheet has essentially consistent thickness and density across the entire surface.

SUMMARY OF INVENTION

Technical Problem

In ordinary absorbent articles, it is desirable for the nonwoven fabric of the top sheet to have low density and numerous gaps between fibers (i.e., allowing fluids to readily permeate without accumulating), so that the region in contact with the site of discharge will immediately transmit excreted fluid away from the body and retain it in the absorber. On the other hand, in regions other than the site of discharge (for example, the regions at the rear of the product that contact the buttocks when fitted, or the regions at the sides of the product that contact the inner thigh when fitted), it is desirable to reduce dampness during wear. It is therefore desirable for the top sheet around the periphery to be such as to reduce the distance between the skin and the absorber (i.e., it should have a low thickness and few gaps between fibers) so that sweat and water vapor transpiring from the skin are rapidly transported to and held in the absorber and do not collect between the body and the top sheet, in order to avoid a damp feel, while it is also desirable for the top sheet in contact with the skin to have few gaps between fibers so that heat from the body does not become trapped therein. This is because such numerous gaps can retain heat. In the prior art examples mentioned above, however, there is no difference between the region in contact with the site of discharge and the other regions in the top sheet composing the absorbent article, and therefore if a thick top sheet with gaps is used, to maximize absorption of excreted fluid, the periphery sections other than the site of discharge have a greater feeling of dampness during use, while if a thin top sheet with narrow gaps is used to minimize the feeling of dampness, the excreted fluid does not migrate as easily to the absorber and the fluid tends to collect inside the nonwoven fabric, resulting in increased accumulation at the surface of the absorbent article and consequent leakage; hence, it has been difficult to achieve both absorption of excreted fluid at the region in contact with the site of discharge, and reduction in damp feel at regions other than those in contact with the site of discharge.

Methods of layering different materials for the region in contact with the site of discharge and the other regions to produce the top sheet have been considered, but using different materials for the region in contact with the site of discharge and the other regions requires the use of an extra material as well as a layering operation, thus further complicating the process through more steps and increasing potential loss due to shifting of the layers. Trim loss also increases, as the region that contacts with the site of discharge must be cut.

Solution to Problem

It is an object of the present invention to provide an absorbent article comprising a top sheet that can be obtained by in-line processing of a nonwoven fabric composed of a single sheet and having uniform physical properties (thickness and density) so as to avoid trim loss and product loss and without complicating the production process, and which achieves both permeability for excreted fluid at the region in contact with the site of discharge and a reduced feeling of dampness at the regions other than those in contact with the site of discharge.

The invention relates to an absorbent article comprising a liquid-permeable top sheet, a liquid-impermeable back sheet, and an absorber sandwiched between the top sheet and back sheet, wherein the top sheet is composed of a nonwoven fabric, and the region of the top sheet that contacts the site of discharge is the low density section of the nonwoven fabric with a lower apparent density than the other regions of the top sheet.

In the absorbent article of the invention, the thickness of the low density section of the top sheet is preferably larger than the thickness of the sections other than the low density section of the top sheet.

In the absorbent article of the invention, the basis weight of the low density section of the top sheet is preferably the same as the basis weight of the sections other than the low density section of the top sheet.

The absorbent article of the invention preferably has thermocompression bonded sections interspersed at the sections other than the low density section of the top sheet.

The absorbent article of the invention preferably has a pair of compressed grooves formed along both sides in at least the lengthwise direction of the absorbent article, with the low density section of the top sheet situated between the pair of compressed grooves.

The method of the invention is a method for producing an absorbent article comprising a liquid-permeable top sheet, a liquid-impermeable back sheet and an absorber sandwiched between the top sheet and back sheet, which method comprises heat treating the discharge site-contacting region of the top sheet which is composed of a nonwoven fabric, to form a top sheet wherein the discharge site-contacting region of the top sheet is the low density section with a lower apparent density of the nonwoven fabric compared to the other regions of the top sheet, and layering the top sheet on which the low density section has been formed, onto the back sheet and absorber.

Advantageous Effects of Invention

The absorbent article of the invention allows body fluid to smoothly migrate to the absorber without accumulating and spreading on the top sheet, thus avoiding leakage and the fear of leakage, while also absorbing sweat transpiring from the body to avoid trapping of heat and preventing damp feel during use. The absorbent article of the invention allows the top sheet to be obtained by processing in a single step, thereby reducing trim loss of the material that occurs in sheet layering steps, and rendering the manufacturing line more compact and simple, while also lowering equipment cost.

DESCRIPTION OF EMBODIMENTS

Figure 1:
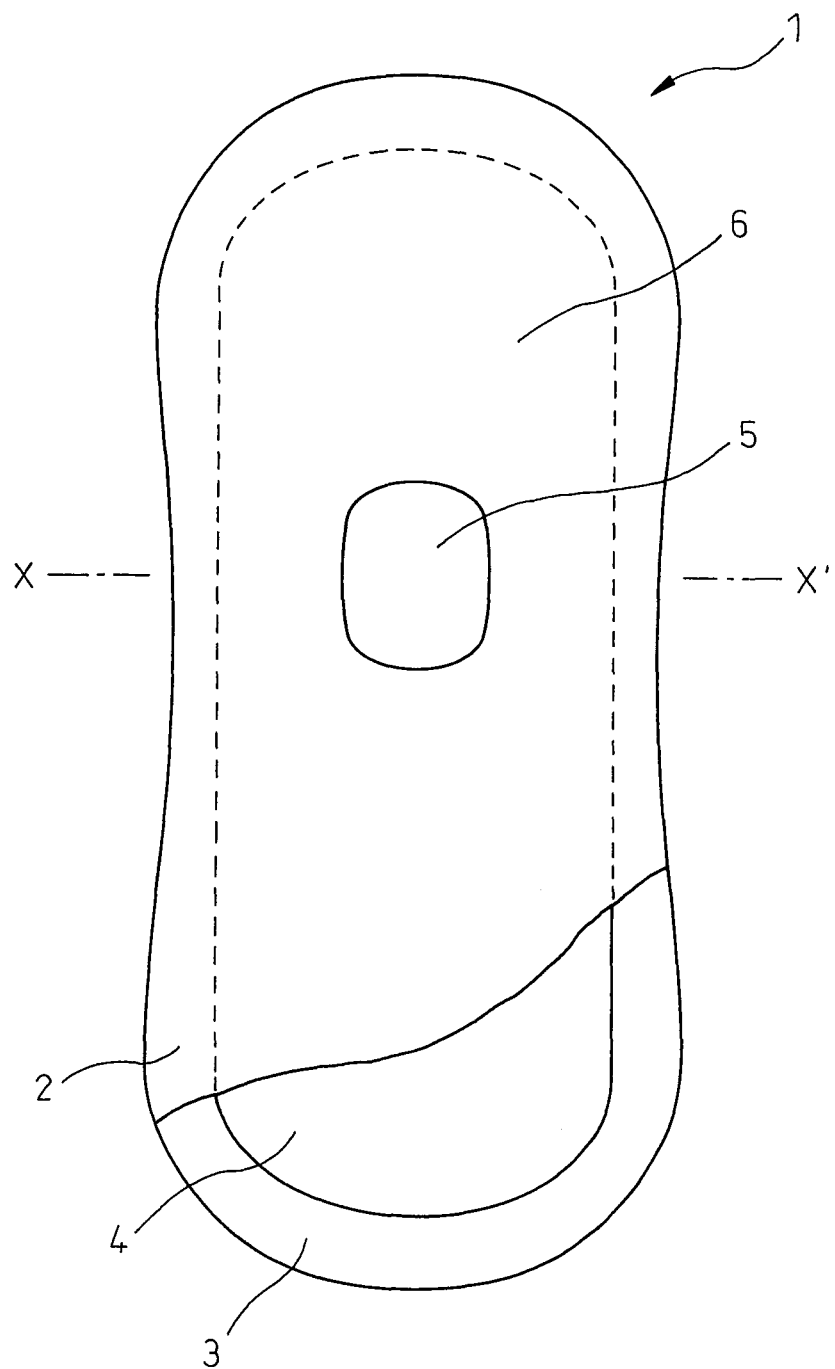
FIG. 1 is a plan view of the first example of the absorbent article of the invention.
Figure 2:
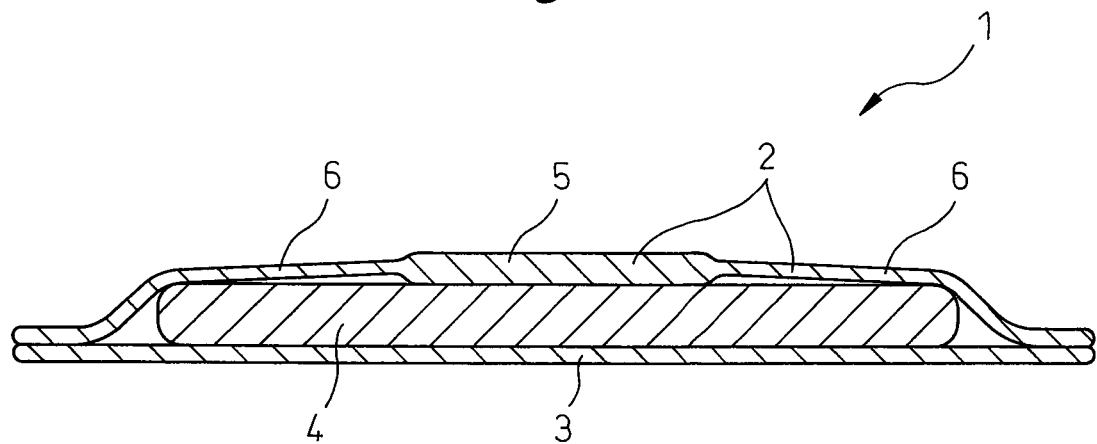
FIG. 2 is a cross-sectional view of the first example of the absorbent article of the invention.

The invention will now be described in greater detail with reference to the accompanying drawings, with the understanding that the invention is not limited to the examples depicted in the drawings.
FIG. 1 is a plan view of a first example of an absorbent article according to the invention, and FIG. 2 is a cross-sectional view of the same along line X-X'. The absorbent article 1 comprises a liquid-permeable top sheet 2, a liquid-impermeable back sheet 3 and an absorber 4, the absorber 4 being sandwiched between the top sheet 2 and back sheet 3. A portion of the top sheet 1 is cut away in FIG. 1. The top sheet 2 is composed of a nonwoven fabric. The top sheet 2 is divided into two sections, the region 5 in contact with the site of discharge and the other region 6. The region 5 that contacts with the site of discharge of the user, when the user wears the absorbent article 1, has a lower apparent density of the nonwoven fabric than the other region 6. That is, the region 5 of the top sheet in contact with the site of discharge is the low density section. On the other hand, the region 6 of the top sheet other than the region in contact with the site of discharge is the "high-density section". The simple term "density" will hereinafter refer to the apparent density of the nonwoven fabric. A top sheet having the low density section 5 and the high density section 6 is composed of a single sheet, but the low density section 5 has a lower density and a larger thickness than the high density section 6, also with more gaps between the fibers composing the nonwoven fabric. Conversely, the high density section 6 has a smaller thickness, higher density and more gaps between fibers composing the nonwoven fabric, compared to the low density section 5. The simple term "gaps" will hereinafter refer to the gaps between fibers composing the nonwoven fabric. A large thickness of the low density section 5 will reduce backflow of fluid when the absorbent article is subjected to body pressure. Since the low density section 5 and high density section 6 are obtained by working of a single nonwoven fabric sheet, the basis weight of the low density section 5 and the basis weight of the high density section 6 are identical, if microscopic variation in basis weight during fabrication of the nonwoven fabric is ignored.

To avoid slippage during wear, the low density section 5, i.e. the region of the top sheet in contact with the site of discharge, is preferably provided at least to a length of between 20 mm and 150 mm and a width of between 10 mm and 70 mm along the center line of the absorbent article 1 at least in the lengthwise direction of the product. More preferably, it is provided to a length of between 50 mm and 130 mm and a width of between 30 mm and 60 mm. If the width and length are too small it will be difficult for the excreted fluid to effectively penetrate when the volume of excreted fluid is large or the wearer has not properly positioned the absorbent article, while if the width and length are too large the area of contact between the low density section and regions other than the site of discharge of the wearer will be increased, causing sweat transpiring from the body to become trapped more easily near the top sheet. The position of the low density section 5 on the product may be in the region including the center of the product, the region corresponding to the wing sections, the region including the sections surrounded by the compressed grooves, and including the narrowest-width sections of the absorber when both sides of the absorber curve inward in the widthwise direction, or the center region of layers of multiple absorbers of different sizes or the bulging section of the absorber where the basis weight of the absorber is greater than at the other regions.

The density of the low density section 5 of the top sheet is approximately equal across the entire low density section 5, if microscopic variation in density during fabrication of the nonwoven fabric is ignored, while the density of the high density section 6 is also approximately equal across the entire high density section 6. The absolute values for the densities are not particularly restricted so long as the density of the low density section 5 is lower than the density of the high density section 6, but preferably the density of the low density section 5 is 0.01-0.04 g/cm$^3$ and the density of the high density section 6 is 0.02-0.10 g/cm$^3$. The density can be determined by dividing the basis weight by the thickness.

The thickness of the low density section 5 of the top sheet is approximately equal across the entire low density section 5 if microscopic variation in thickness during fabrication of the nonwoven fabric is ignored, while the thickness of the high density section 6 is also approximately equal across the entire high density section 6. The absolute values of the thicknesses are not particularly restricted so long as the thickness of the low density section 5 is greater than the thickness of the high density section 6, but preferably the thickness of the low density section 5 is 0.75-3 mm and the thickness of the high density section 6 is 0.3-1.5 mm. The thickness is measured using a KES-FB3 AUTO-A automated compression tester by Kato Tech Corp., after cutting the sample to a size of at least 2 cm².

A process for production of the absorbent article of the invention will now be described.

Figure 3:
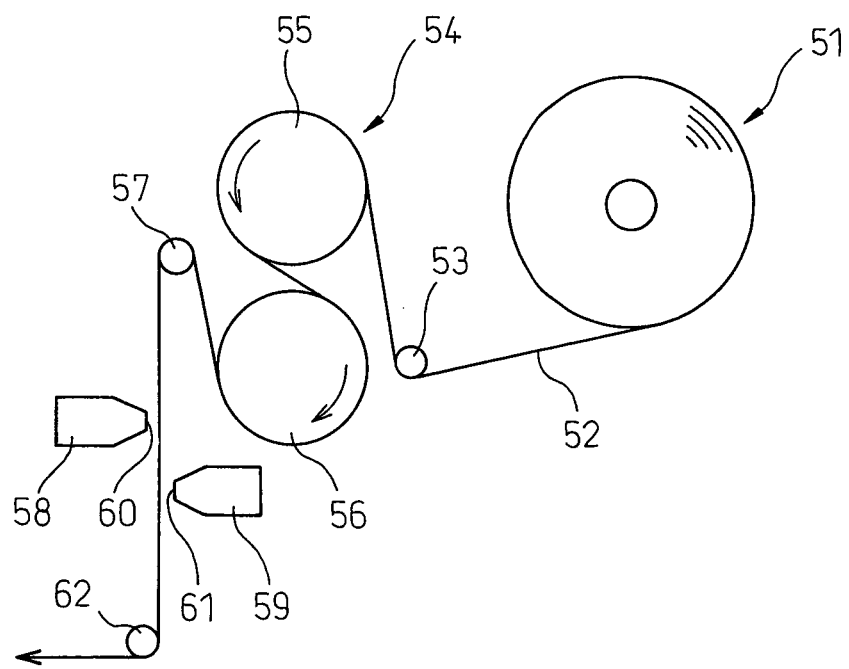
FIG. 3 shows an example of an apparatus for production of a top sheet used in the absorbent article of the invention.
Figure 4:
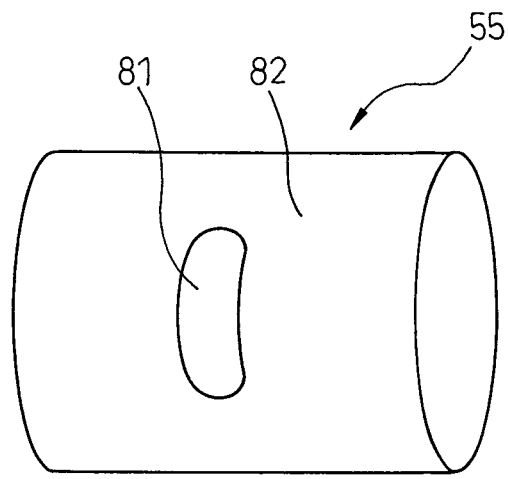
FIG. 4 shows an oblique view of a heated roll used in the apparatus of FIG. 3.

FIG. 3 shows an example of an apparatus for production of a top sheet with a low density section and a high density section, and FIG. 4 shows an oblique view of a roll used in the apparatus.

A nonwoven fabric 52 such as an air-through nonwoven fabric for formation of the top sheet 2 is coiled around a supply fabric roll 51. The nonwoven fabric 52 is coiled around the supply fabric roll 51 with its thickness depressed. The nonwoven fabric 52 passes through a roll 53 and is supplied to a heating unit 54.

The heating, unit 54 is provided with a heated roll 55 and a heated roll 56, and the peripheral surfaces of the heated roll 55 and heated roll 56 comprise a heated section 81 and a non-heated section 82, as shown in FIG. 4. The shape and position of each heated section 81 are designed to correspond to the shape and position of the low density section of the top sheet to be produced. The heated section 81 may be a single section or a plurality of sections. The heated section 81 has a surface formed of a thermal conductive material such as a metal, and the outer periphery surface other than the heated section 81, i.e. the non-heated section 82, is made of a heat insulating material. Such a heated roll may have the section corresponding to the non-heated section 82 covered with a heat insulating material, while leaving open a section corresponding to the heated section 81 on the peripheral surface of the metal roll. The surface temperature of the heated section 81 is set to be above a temperature 50° C. lower than the melting point and not above 5° C. higher than the melting point of the thermoplastic fiber of the nonwoven fabric. It is preferably from the melting point minus 50° C. to the melting point minus 3° C., and more preferably from the melting point minus 30° C. to the melting point minus 5° C. For example, when the nonwoven fabric is an air-through nonwoven fabric formed from polyethylene fiber, the surface temperature of the heated section 81 is preferably about 115° C. The surface temperature of the non-heated section 82 is preferably room temperature.

The heated roll 55 and heated roll 56 are separated from each other, and the nonwoven fabric 52 is transported around the heated rolls 55 and 56 without being subjected to pressure between the heated rolls 55 and 56. During this time, one side of the nonwoven fabric 52 contacts with the surface of the heated roll 55 and is partially heated while the other side of the nonwoven fabric 52 contacts with the surface of the heated roll 56 and is partially heated, so that the nonwoven fabric 52 is partially heated on both the front and back sides by the two heated rolls 55, 56. The heated roll 55 and heated roll 56 are synchronized so that the sections to be heated are equally positioned on the front and back sides. Thus, when the nonwoven fabric 52 is wrapped and transported around the heated roll 55 and heated roll 56, the nonwoven fabric 52 is heated only at the sections in contact with the heated section 81, to obtain a top sheet with partially recovered bulk, or in other words, a top sheet having a low density section and a high density section.

When the nonwoven fabric 52 is an air-through nonwoven fabric composed mainly of thermoplastic fiber, partial heating on the surface of both heated rolls 55 and 56 causes the heated sections of the nonwoven fabric 52 to recover their bulk (thickness) to a range of 1.5-8 fold, and to recover up to ⅓ of their density.

According to the invention, there is no necessary limitation to heating the nonwoven fabric 52 with two heated rolls 55, 56, and for example, it may be heated with only one of the heated rolls 55 or 56. In this case, only one side of the nonwoven fabric 52 will be heated. However, since the effect of bulk recovery of the nonwoven fabric 52 increases with a longer heating time of the nonwoven fabric 52, it is preferred to provide two or more heated rolls. Instead of the construction described above, the nonwoven fabric 52 may be heated by three or more heated rolls, with a separate heated roll being provided in addition to the heated rolls 55 and 56. By thus increasing the number of heated rolls it is possible to lengthen the heating time for the nonwoven fabric 52, thereby increasing the bulk recovery effect at the heated section of the nonwoven fabric 52, and producing a greater difference in density between the low density section and high density section of the top sheet.

The partially bulk-recovered nonwoven fabric 52, i.e., the top sheet with the low density section and high density section, is supplied to the cooling devices 58, 59 via a roll 57. The cooling devices 58, 59 are provided in a pair opposite the front and back sides of the nonwoven fabric 52. The cooling devices 58, 59 blow air from nozzles 60, 61, so that the nonwoven fabric 52 is rapidly cooled on both the front and back sides by the blown air. When the heated and partially bulk-recovered nonwoven fabric 52 is cooled, the fiber forming the nonwoven fabric 52 becomes immobilized in a short period of time, thus allowing the nonwoven fabric 52 to immediately hold its bulk-recovered state. The cooled nonwoven fabric 52 is then transported around a roll 62 to the following step.

Figure 5:
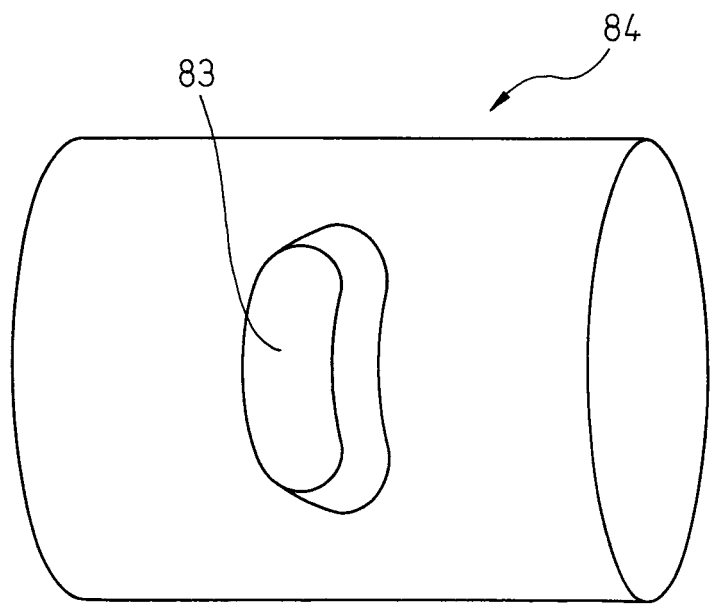
FIG. 5 shows an oblique view of a different heated roll used in the apparatus of FIG. 3.
Figure 6:
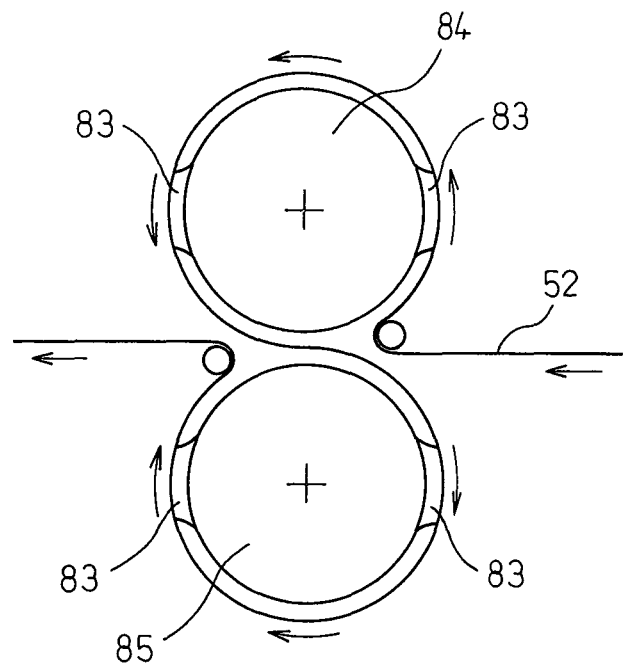
FIG. 6 shows an example of a heating unit employing the heated roll of FIG. 5.

A heated roll 84 with a protrusion 83 such as shown in FIG. 5 may be used instead of the heated rolls 55, 56 with the heated section 81 and non-heated section 82 on the peripheral surface. FIG. 6 shows an example of a heating unit employing such a heated roll. The heating unit is composed of two heated rolls 84, 85. The shapes and positions of their protrusions 83 are designed to correspond to the shape and position of the low density section of the top sheet to be produced. One or a plurality of protrusions 83 may be provided. The nonwoven fabric 52 is passed around the heated rolls 84, 85, as shown in FIG. 6. The heated rolls 84, 85 with protrusions 83 are heated, and the temperature of the surface of the protrusions 83 is set to be below the melting point of the thermoplastic fiber of the nonwoven fabric and above a temperature 50° C. lower than the melting point, and preferably from the melting point minus 50° C. to the melting point minus 3° C., and more preferably from the melting point minus 30° C. to the melting point minus 5° C. When the nonwoven fabric 52 passes around the periphery of the rolls 84, 85, the nonwoven fabric 52 passes in contact only with the protrusions 83, so that the bulk of the nonwoven fabric 52 is recovered only at the region in contact with the protrusions 83 and the obtained top sheet has a low density section and a high density section. In the apparatus of FIG. 6, two rolls are provided and the nonwoven fabric 52 is passed through in an S-shaped path, but the number of rolls, their diameters and materials and the fabric path are not restricted so long as the desired difference in density is obtained.

Figure 7:
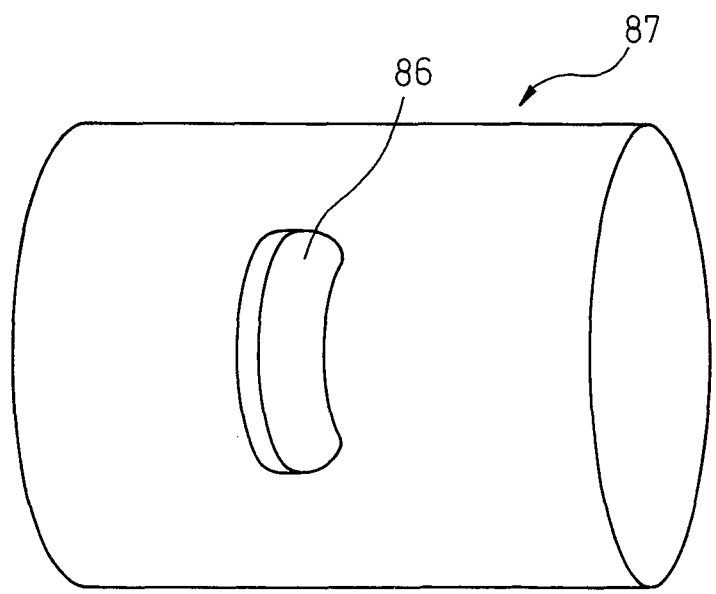
FIG. 7 shows an oblique view of yet a different heated roll used in the apparatus of FIG. 3.
Figure 8:
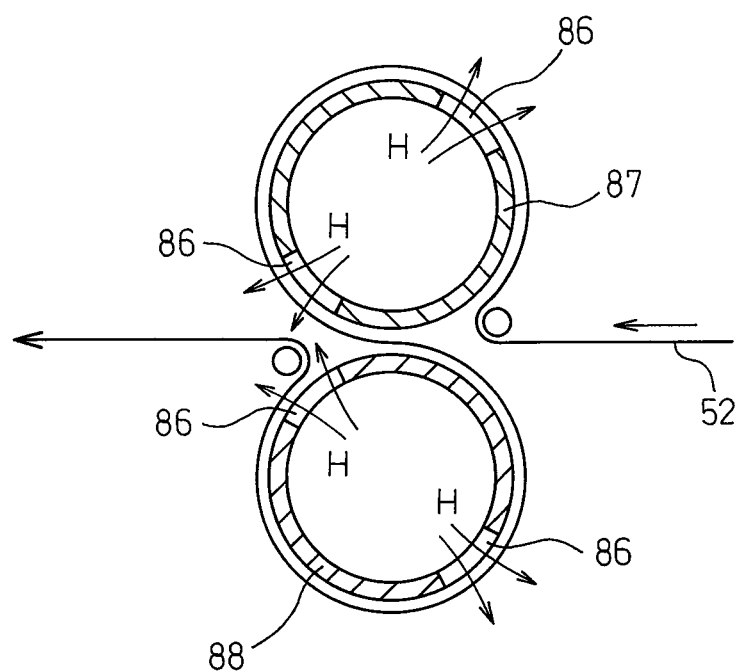
FIG. 8 shows an example of a heating unit employing the heated roll of FIG. 7.

A roll 87 with a hot air-blowing hole 86, such as shown in FIG. 7, may also be used instead of the heated rolls 55, 56, 84, 85. FIG. 8 shows an example of a heating unit employing such a heated roll. The heating unit is composed of two heated rolls 87, 88 each with a hot air-blowing hole 86. The shape and position of each hot air-blowing hole 86 is designed to correspond to the shape and position of the low density section of the top sheet to be produced. A single hot air-blowing hole 86 or a plurality thereof may be provided. The nonwoven fabric 52 is passed around the rolls 87, 88, as shown in FIG. 8. When the nonwoven fabric 52 is passed around the rolls 87, 88, hot air H is blown from the interior of the rolls 87, 88 through the hot air-blowing holes 86, and the hot air H is blown onto the nonwoven fabric 52, thus recovering the bulk of the nonwoven fabric 52 only at the sections corresponding to the hot air-blowing holes 86, to obtain a top sheet with a low density section and a high density section. The temperature of the hot air H which is blown is between a temperature 50° C. lower than the melting point of the thermoplastic fiber of the nonwoven fabric and a temperature 5° C. higher than the melting point, preferably in a range from the melting point minus 50° C. to the melting point minus 3° C., and more preferably in a range from the melting point minus 30° C. to the melting point minus 5° C. In the apparatus of FIG. 8, two rolls are provided and the nonwoven fabric 52 is passed through in an S-shaped path, but the number of rolls, their diameters and materials and the fabric path are not restricted so long as the desired difference in density is obtained. If reflector plates are provided sandwiching the nonwoven fabric on the outside of the rolls, the heat from the blowing holes will be reflected onto the reflector plates, thus allowing the bulk at the sections corresponding to the blowing holes to be recovered more efficiently. The hot air H blown onto the nonwoven fabric 52 may be allowed to pass naturally through the nonwoven fabric 52, or a suction device may be provided on the outside of the rolls to draw the hot air H through by suction force.

The low density section may also be formed using far-infrared rays instead of heated rolls. In this case, a masking shield having a far-infrared ray-permeable region corresponding to the low density section to be formed may be placed between the far-infrared ray source and the nonwoven fabric so that the far-infrared rays are irradiated only on the region where the low density section is to be formed, and the nonwoven fabric then exposed to the far-infrared rays to heat only the region where the low density section is to be formed, thereby obtaining a top sheet with a low density section and a high density section.

The absorber and back sheet are then layered on the top sheet with the low density section and high density section produced in the manner described above and bonded by pin embossing or the like and then cut to the desired shape to obtain an absorbent article of the invention.

The top sheet of this example has low density at the region of the top sheet that contacts with the site of discharge of the user during use, and since the distance between fibers is wider in this region, excreted fluid readily permeates and immediately migrates to the absorber. When the bulk of the nonwoven fabric has been recovered, the direction (orientation) of the fibers is in the thickness direction, and therefore excreted fluid migrates more easily downward along the fibers in the low density section of the top sheet. Consequently, minimal leakage occurs because the excreted fluid does not accumulate inside the top sheet and hence is absorbed as a spot without spreading over the surface of the product. On the other hand, since the top sheet has a small thickness in the regions contacting with areas other than the site of discharge of the user during use, the distance between the body surface and the absorber of the product is shorter and sweat (vapor) transpiring from the body rapidly passes through the top sheet and is absorbed into the absorber, thereby preventing buildup of sweat on the skin surface that causes a sticky feel. In addition, since the density is high and the distance between fibers is shorter, there are fewer gaps inside the nonwoven fabric and entrapment of heat from the body can be reduced. Elimination of stickiness caused by sweat and entrapment of heat helps to avoid a feeling of dampness during use. These effects improve the liquid permeability of the region that will contact with the site of discharge of a user, by simple working of a single nonwoven fabric with a uniform thickness and density on a manufacturing line, to obtain a top sheet for an absorbent article that reduces the feeling of dampness in regions that contact with areas other than the site of discharge.

A second example of an absorbent article according to the invention will now be described.

Figure 9:
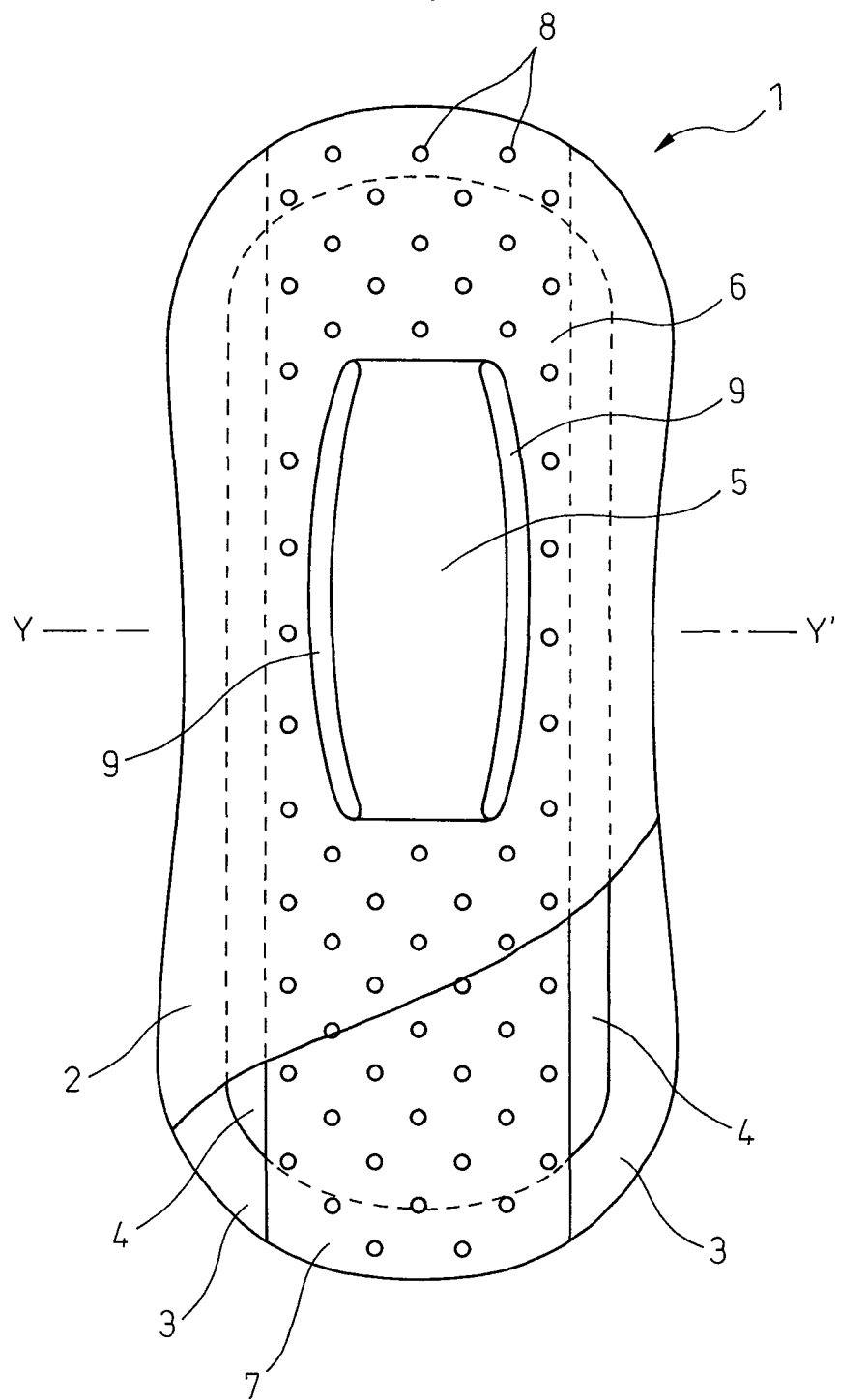
FIG. 9 is a plan view of the second example of the absorbent article of the invention.
Figure 10:
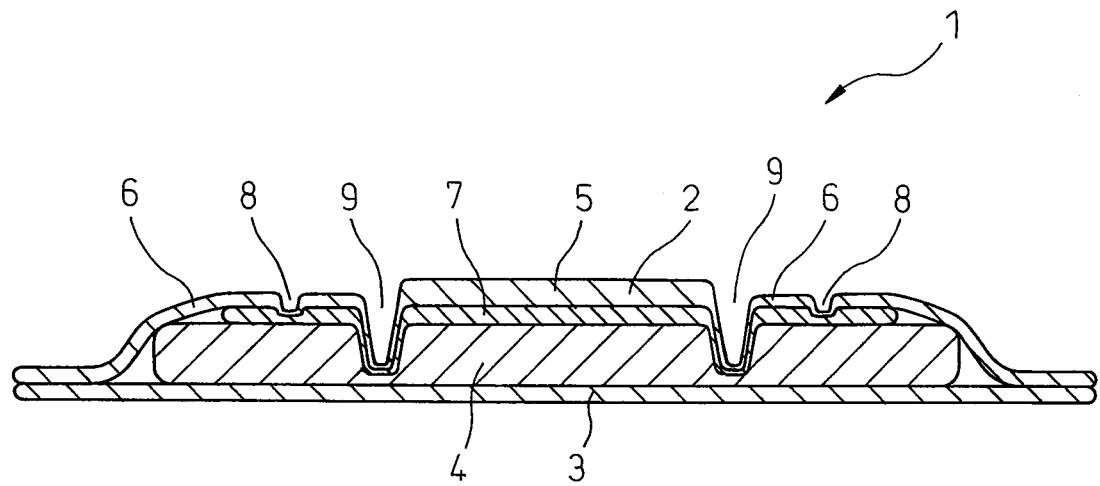
FIG. 10 is a cross-sectional view of the second example of the absorbent article of the invention.

FIG. 9 is a plan view of a second example of an absorbent article according to the invention, and FIG. 10 is a cross-sectional view of the same along line Y-Y'. The absorbent article 1 comprises a liquid-permeable top sheet 2, a liquid-permeable second sheet 7, an absorber 4 and a liquid-impermeable back sheet 3. A portion of the top sheet 2 is cut away in FIG. 9.

The top sheet 2 has a low density section 5 and a high density section 6. The low density section 5 is formed in the region that contacts with the site of discharge of the user when the user wears the absorbent article 1. The top sheet is composed of a single sheet, but the low density section 5 has a lower density and a larger thickness than the high density section 6, also with more gaps between the fibers composing the nonwoven fabric. The basis weight of the low density section 5 and the basis weight of the high density section 6 are identical, if microscopic variation in basis weight during fabrication of the nonwoven fabric is ignored.

In this second example of the absorbent article, the second sheet 7 is provided between the top sheet 2 and absorber 4. The second sheet 7 is composed of a nonwoven fabric with a higher density than the nonwoven fabric composing the top sheet 2, and it has a smaller width than the width of the top sheet 2. Since fluids will tend to migrate toward the areas of higher density, a second sheet with a higher density than the top sheet is provided, thereby helping to promote absorption of fluid discharged from the body and prevent return of absorbed fluids.

In the second example of the absorbent article, thermocompression bonded sections 8 are interspersed in the high density section 6 of the top sheet 2. The thermocompression bonded sections 8 may be formed by heat embossing of the laminate of the top sheet 2 and second sheet 7. If the thermocompression bonded sections 8 are interspersed in the high density section 6 of the top sheet 2, sweat (vapor) transpiring from the body permeates more easily through the thermocompression bonded sections 8 since the thermocompression bonded sections 8 are thinner, thus promoting transmission of sweat (vapor) transpiring from the body, while the reduced number of gaps inside the nonwoven fabric help further reduce entrapment of heat from the body.

The thermocompression bonded sections 8 may also be interspersed in the low density section 5 of the top sheet 2. If the thermocompression bonded sections 8 are interspersed in the low density section 5, fluid will migrate more easily into the absorber when the top sheet 2 and second sheet 7 are bonded. If the thermocompression bonded sections 8 interspersed in both the high density section 6 and low density section 5, the number of thermocompression bonded sections 8 per unit area is preferably greater in the high density section 6 than in the low density section 5.

Figure 11:
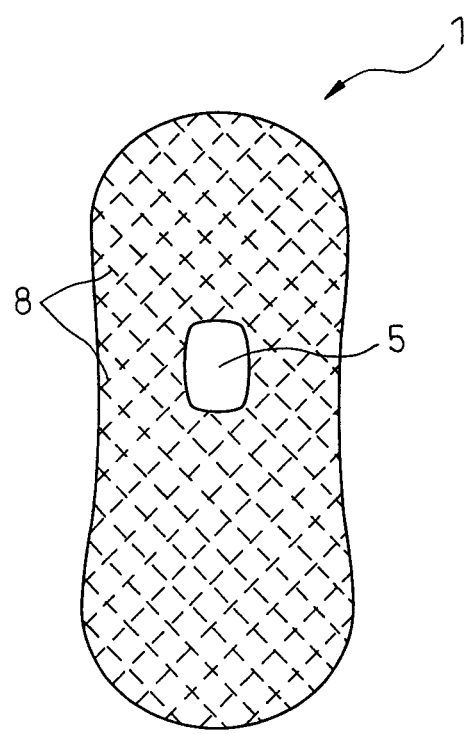
FIG. 11 shows an example of the arrangement of thermocompression bonded sections interspersed in the high density section.

The shapes, dimensions and arrangement of the interspersed thermocompression bonded sections 8 may be as desired so long as the effect of the invention is not impaired. The shapes of the thermocompression bonded sections 8 are not particularly restricted and may be circular, ellipsoid, square, rectangular, rhomboid, star-shaped, heart-shaped or the like. The dimensions preferred for the thermocompression bonded sections 8 will depend on the shapes but may be, for example, 0.5 mm-15 mm. The arrangement of the thermocompression bonded sections 8 is not particularly restricted, but may be staggered, lattice-shaped, linear, curved or the like. A plurality of broken lines may be arranged in parallel in two directions as shown in FIG. 11, for example.

In the second example of the absorbent article, a pair of compressed grooves 9 are formed at least along both sides in the lengthwise direction of the absorbent article, sandwiching both edges of the low density section 5 of the top sheet. The compressed grooves may be formed by layering the top sheet on the absorber and embossing the layers. The pair of compressed grooves 9 shown in FIG. 9 are two separate grooves, but the pair of compressed grooves may be connected and surrounding the low density section 5, or two or more pairs of compressed grooves may be provided. If compressed grooves are provided, the sections of the compressed grooves of the absorbent article will bend when the user wears the absorbent article, thereby expanding the center of the absorbent article and bringing the low density section 5 of the top sheet closer to the site of discharge of the user, thus further promoting penetration of excreted fluid.

When a pair of compressed grooves are formed at least along both sides in the lengthwise direction of the absorbent article, the low density section of the top sheet need only be present at least between the pair of compressed grooves, but it may also be present outside of the area between the pair of compressed grooves. For example, the low density section may extend outside of the pair of compressed grooves. The compressed grooves may also be formed to surround the area near the center of the absorbent article, and a more prominent effect can be achieved if absorbers of different sizes are layered near the center section or if the basis weight is increased with respect to the other regions.

A process for production of the second example of the absorbent article will now be described.

The top sheet with a low density section and high density section used for the second example of the absorbent article can be produced in the same manner as the first example. If a second sheet is layered on the top sheet comprising the low density section and high density section and the layers are subjected to embossing from the top sheet side, the top sheet will become bonded with the second sheet while simultaneously forming the multiple interspersed thermocompression bonded sections in the laminate. The top sheet/second sheet laminate obtained in the manner described above is layered on the absorber. The layering is accomplished in such a manner that the second sheet and absorber are in contact. The laminate comprising the top sheet, second sheet and absorber is subjected to embossing from the top sheet side to form compressed grooves. The laminate comprising the top sheet, second sheet and absorber, on which the compressed grooves have been formed, is then layered onto the back sheet. This layering is accomplished in such a manner that the absorber and back sheet are in contact. The sections of the four-layer laminate where the top sheet and back sheet are in contact are subjected to embossing and hot-melt adhesive treatment, to accomplish bonding between the top sheet and back sheet. The laminate is finally cut to the desired shape to obtain an absorbent article according to the invention.

In the process described above, the second sheet was layered and bonded after forming the low density section and high density section in the top sheet, but the low density section and high density section may be formed on the top sheet by working the laminate in the same manner as the first example, after the second sheet has been layered and bonded onto the top sheet on which the low density section and high density section have not yet been formed. Since the low density section and high density section will also be formed on the second sheet in this case, the effect of the invention will be increased.

A third example of an absorbent article according to the invention will now be described.

Figure 12:
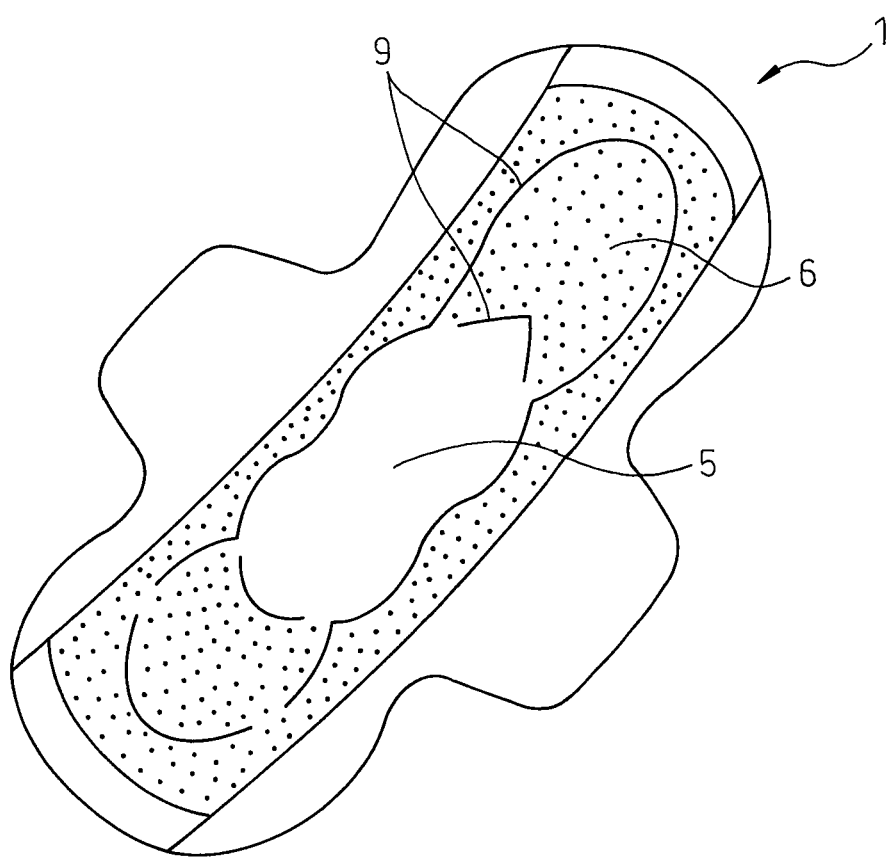
FIG. 12 is an oblique view of the second example of the absorbent article of the invention.
Figure 13:
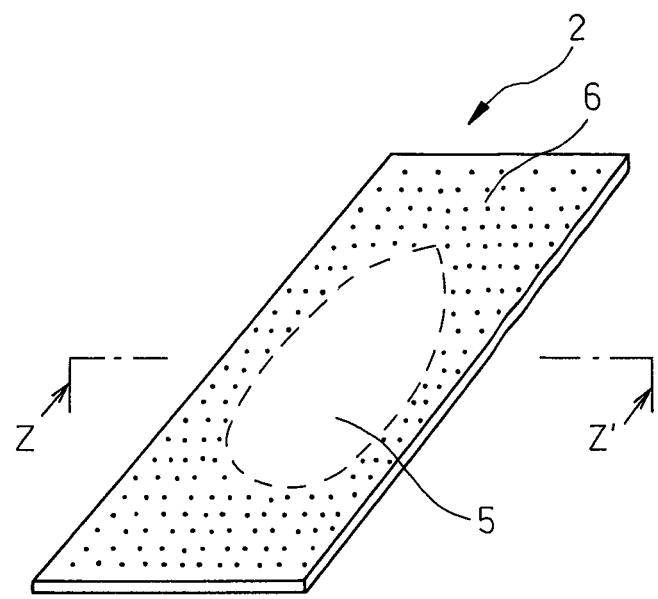
FIG. 13 is an oblique view of the top sheet used in the third example of the absorbent article of the invention.
Figure 14:
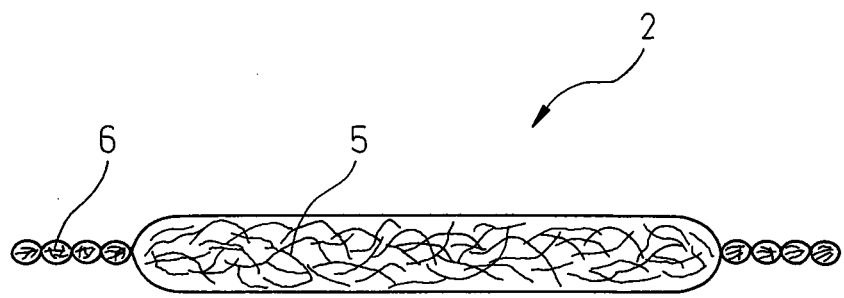
FIG. 14 is a cross-sectional view of the top sheet used in the third example of the absorbent article of the invention.

FIG. 12 is an oblique view of the absorbent article 1 of the third example of the invention, FIG. 13 is an oblique view of the top sheet 2 used in the absorbent article 1, and FIG. 14 is a cross-sectional view of the top sheet 2 along line Z-Z'.

As the reverse of the first example, the top sheet 2 of this example is obtained by reducing the bulk in the region 6 outside the region in contact with the site of discharge of the user, and although the low density section 5 and high density section 6 are composed only of a single nonwoven fabric, the low density section 5 has a larger thickness, a lower density and more gaps than the high density section 6. Conversely, the high density section 6 has a smaller thickness, higher density and fewer gaps between fibers than the low density section 5.

Figure 15:
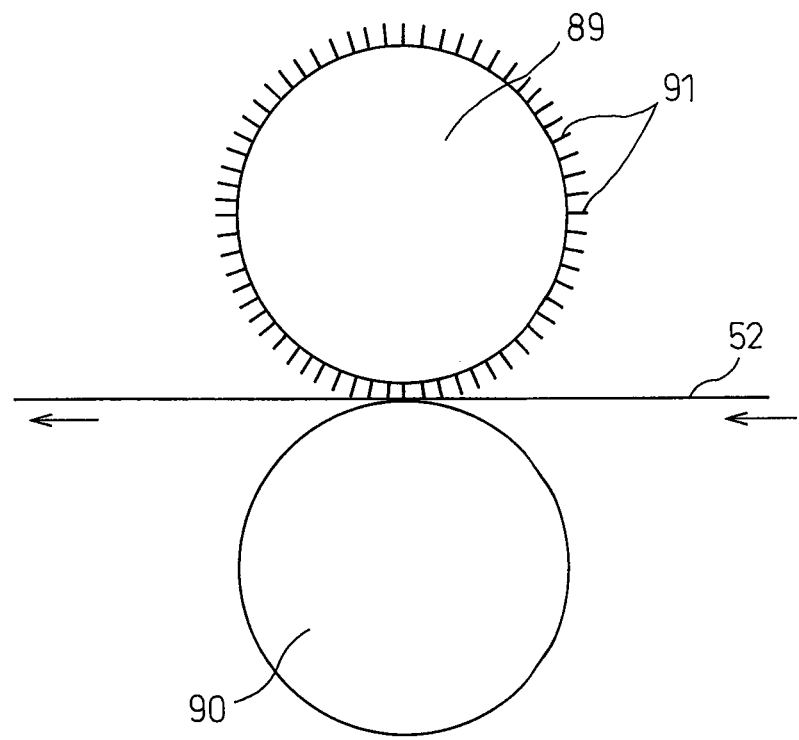
FIG. 15 shows an example of an apparatus for production of the top sheet used in the third example of the absorbent article of the invention.
Figure 16:
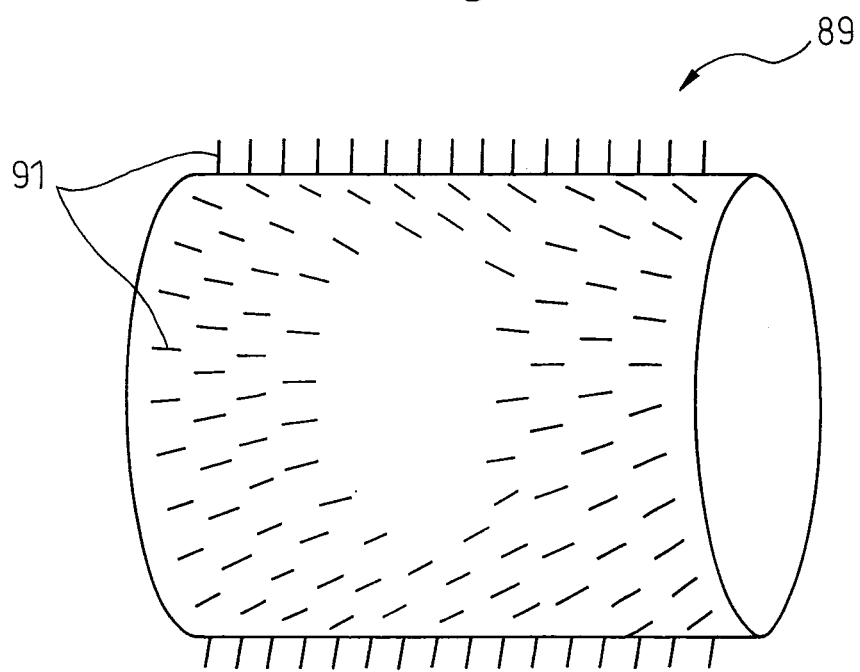
FIG. 16 shows an oblique view of the roll used in the apparatus of FIG. 15.

The top sheet 2 of this example can be produced in the following manner. FIG. 15 shows an example of an apparatus for production of the top sheet 2. FIG. 16 is an oblique view of a roll used in the apparatus. The nonwoven fabric 52 is passed between the upper roll 89 and lower roll 90. As shown in FIG. 16, the upper roll 89 is provided with numerous protrusions 91. When the nonwoven fabric 52 is passed between the upper roll 89 and lower roll 90, the region of the nonwoven fabric 52 corresponding to the high density section 6 is compressed and melt molded by the heated protrusions 91, while the region corresponding to the low density section 5 is not compressed. In FIG. 16, the upper roll 89 has a zigzag arrangement of circular pin shapes while the lower roll is flat, but so long as the effect of the invention can be obtained, the protrusions 91 of the upper roll 89 may be in a lattice arrangement, or in an oblique, lateral or longitudinal arrangement, and the pin shapes may be polygonal, such as quadrilateral, or star-shaped, instead of circular. The lower roll 90 does not need to be flat, and both the upper roll 89 and lower roll 90 may have patterns. The upper roll may also be one provided with recesses on the peripheral surface of the roll in the region corresponding to the low density section, instead of the upper roll 89. In this case, the nonwoven fabric is compressed only at the section where the high density section is to be formed, for production of a top sheet with a low density section and high density section. So long as the effect of the invention is obtained, the number and diameters of the rolls and the method of passing the material through may be as desired.

The shape of the absorbent article of the invention is not particularly restricted so long as it is a shape suited for the female body and panties, such as, in the case of a sanitary napkin, rectangular, elliptical, gourd-shaped, or provided with "wings" to prevent slippage within panties. The total outer dimension is preferably 100-500 mm and more preferably 150-350 mm in the lengthwise direction. In the widthwise direction it is preferably 30-200 mm and more preferably 40-180 mm. The dimension of the absorber in the lengthwise direction is preferably 90-490 mm and more preferably 140-340 mm. The dimension of the absorber in the widthwise direction is preferably 25-100 mm and more preferably 35-80 mm.

Nonwoven fabrics for the top sheet include, but are not limited to, nonwoven fabrics formed by a carding method, nonwoven fabrics formed by a heat sealing method, nonwoven fabrics formed by a hydroentangling method, nonwoven fabrics formed by a needle punching method, nonwoven fabrics formed by a solvent bonding method, nonwoven fabrics formed by a spunbond method, nonwoven fabrics formed by a meltblown method, and air-through nonwoven fabrics. Air-through nonwoven fabrics are preferred among these. The fibers composing the nonwoven fabric are not particularly restricted, and there may be mentioned thermoplastic resin fibers including polyolefins such as polyethylene or polypropylene, polyesters such as polyethylene terephthalate, and polyamides, or core-sheath type, core-sheath eccentric type or side-by-side type composite fibers comprising these resins. In order to control the wettability, a hydrophilic or water-repellent agent may be coated onto or incorporated into the fiber surface. From the viewpoint of hydrophilicity for body fluids, there may be included cellulose-based hydrophilic fibers such as pulp, chemical pulp, rayon, acetate or natural cotton. The fiber used is preferably 1.1-6.6 dtex and the basis weight is preferably adjusted to the range of 15-120 $g/m^2$.

When a second sheet is provided, the nonwoven fabric for the second sheet may be the same type of nonwoven fabric used for the top sheet, but the density must be larger than that of the top sheet.

The liquid-impermeable back sheet of the absorbent article of the invention has the function of preventing outside leakage of fluids such as menstrual blood and urine that have been absorbed by the absorber, and therefore the material used is one that can prevent outside leakage of such fluids. If the material used prevents passage of fluids but is air permeable, it will be possible to reduce dampness during wear and alleviate unpleasantness during wear. As examples of such materials there may be mentioned liquid-impermeable films composed mainly of polyethylene (PE) or polypropylene (PP), air-permeable films, and composite sheets obtained by laminating a liquid-impermeable film onto one side of a spunbond or other type of nonwoven fabric. It is preferred to use a hydrophobic nonwoven fabric, an impermeable plastic film or a laminate sheet comprising a nonwoven fabric and an impermeable plastic film. The material may also be an SMS nonwoven fabric obtained by sandwiching a meltblown nonwoven fabric with high water resistance between high-strength spunbond nonwoven fabrics.

The absorber in the absorbent article of the invention has the function of absorbing and retaining fluids such as menstrual blood and urine, and preferably it has high bulk, is resistant to deformation and has low chemical irritability. An example is an absorber composed of fluffy pulp or an airlaid nonwoven fabric, and a super absorbent polymer. Instead of fluffy pulp there may be used, for example, chemical pulp, cellulose fiber, or artificial cellulose fiber such as rayon or acetate. For example, a mixture of pulp with a basis weight of 500 $g/m^2$ and a polymer with a basis weight of 20 $g/m^2$ (the polymer being dispersed throughout), where the pulp and polymer are uniformly distributed throughout, may be packed in a tissue with a basis weight of 15 $g/m^2$. An example of an airlaid nonwoven fabric is a nonwoven fabric comprising pulp and synthetic fiber either heat sealed or fixed with a binder. A super absorbent polymer (SAP) has three-dimensional network structure with an approximately crosslinked water-soluble polymer and therefore absorbs a few hundred to a few thousand times its weight of water, but it is essentially water-insoluble and the absorbed water does not emerge even with a certain degree of pressure application; examples thereof include starch-based, acrylic acid-based and amino acid-based particulate or fibrous polymers. The shape and structure of the absorber may be varied if necessary, but the total absorption by the absorber must be suitable for the designed insertion volume and the desired use of the absorbent article. The size and absorption performance of the absorber will also vary depending on the intended use.

INDUSTRIAL APPLICABILITY

The absorbent article of the invention can be used as sanitary napkins, disposable diapers or the like.

REFERENCE SIGNS LIST

1 Absorbent article
2 Top sheet
3 Back sheet
4 Absorber
5 Low density section
6 High density section
7 Second sheet
8 Thermocompression bonded section
9 Compressed groove
51 Supply fabric roll
52 Nonwoven fabric
53 Roll
54 Heating unit
55, 56 Heated roll
57 Roll
58, 59 Cooling devices
60, 61 Nozzle
81 Heated section
82 Non-heated section
83 Protrusion
84, 85 Heated rolls
86 Hot air blowing hole
87, 88 Rolls
89 Upper roll
90 Lower roll
91 Protrusion

The invention claimed is:

1. An absorbent article comprising a liquid-permeable top sheet, a liquid-impermeable back sheet, and an absorber sandwiched between the top sheet and back sheet, wherein the top sheet is composed of a nonwoven fabric, and a region of the top sheet that contacts a site of discharge is a low density section of the nonwoven fabric with a lower apparent density than the other regions of the top sheet, wherein
a top surface of the low density section of the top sheet defines a highest point of the top sheet,
the top sheet consists of one low density section and one high density section, and
the low density section is surrounded by the high density section.

2. An absorbent article according to claim 1, wherein the thickness of the low density section of the top sheet is larger than the thickness of the sections other than the low density section of the top sheet.

3. An absorbent article according to claim 1, wherein the basis weight of the low density section of the top sheet is the same as the basis weight of the sections other than the low density section of the top sheet.

4. An absorbent article according to claim 1, wherein thermocompression bonded sections are interspersed at the sections other than the low density section of the top sheet.

5. An absorbent article according to claim 1, wherein a pair of compressed grooves are formed along both sides in at least the lengthwise direction of the absorbent article, and the low density section of the top sheet is situated between the pair of compressed grooves.

6. An absorbent article according to claim 1, wherein a second sheet arranged between the top sheet and the absorber, and wherein the second sheet has a higher density than that of the top sheet.

7. An absorbent article according to claim 1, wherein the top sheet and the second sheet are bonded at thermocompression bonded sections at remaining sections of the top sheet other than at the low density section of the top sheet.

8. An absorbent article according to claim 1, wherein the second sheet has a low density section corresponding to the low density section of the top sheet and having a lower apparent density than remaining sections of the second sheet.

* * * * *